United States Patent [19]

Denny et al.

[11] Patent Number: 5,750,782
[45] Date of Patent: May 12, 1998

[54] NITROANILINE DERIVATIVES AND THEIR USE AS ANTI-TUMOUR AGENTS

[75] Inventors: William Alexander Denny; Brian Desmond Palmer; William Robert Wilson, all of Auckland, New Zealand

[73] Assignee: Cancer Research Campaign Technology Limited, London, England

[21] Appl. No.: 685,079

[22] Filed: Jul. 23, 1996

Related U.S. Application Data

[62] Division of Ser. No. 244,449, filed as PCT/GB92/02199, Nov. 27, 1992, Pat. No. 5,571,845.

[51] Int. Cl.$^6$ .................................................. C07C 233/65
[52] U.S. Cl. .................................. 564/166; 564/163
[58] Field of Search .................................. 564/166, 163

[56] References Cited

U.S. PATENT DOCUMENTS 5,171,889  12/1992  Anderson ............................... 564/166

OTHER PUBLICATIONS

Palmer et al., "Hypoxia–Selective . . . Cells", J. or Medicinal Chemistry, vol. 35, No. 17, pp. 3214–3222., Aug. 1992.

*Primary Examiner*—Gary Geist
*Assistant Examiner*—Rosalynd A. Keys
*Attorney, Agent, or Firm*—Pennie & Edmonds LLP

[57] ABSTRACT

The invention provides nitroaniline derivatives represented by general formula (1) where the nitro group is substituted at any one of the available benzene positions 2-6; where R and A separately represent the groups $NO_2$, $CN$, $COOR^1$, $CONR^1R^2$, $CSNR^1R^2$ or $SO_2NR^1R^2$ and A is substituted at any one of the available benzene positions 2-6; where B represents $N(CH_2CH_2halogen)_2$ or $N(CH_2CH_2OSO_2R^3)_2$ substituted at any one of the available benzene positions; and where $R^1$, $R^2$ and $R^3$ separately represent H, or lower alkyl optionally substituted with hydroxyl, ether, carboxy or amino functions, including cyclic structures, or $R^1$ and $R^2$ together with the nitrogen form a heterocyclic structure, and pharmaceutical preparations containing them. These compounds have activity as hypoxia-selective cytotoxins, reductively-activated prodrugs for cytotoxins, hypoxic cell radiosensitisers, and anticancer agents.

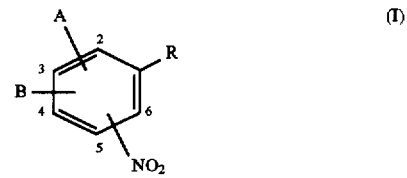

(I)

4 Claims, 1 Drawing Sheet

FIG. 1

NITROANILINE DERIVATIVES AND THEIR USE AS ANTI-TUMOUR AGENTS

This is a division of application Ser. No. 08/244,449, filed as PCT/GB92/02199 Nov. 27, 1992, U.S. Pat. No. 5,571,845.

Alkylating agents are an important class of anticancer drugs, which express their cytotoxic and antitumour effects by forming adducts with cellular DNA (Garcia et al., *Biochem. Pharmacol*, 1988, 37, 3189).

The present invention relates to novel nitroaniline-based alkylating agents having activity as hypoxia-selective cytotoxins, reductively-activated prodrugs for cytotoxins, hypoxic cell radiosensitisers, and anticancer agents to methods of preparing the novel compounds, and to the use of these compounds as antitumour agents.

In one aspect, the present invention relates to the class of nitroaniline derivatives represented by the general formula (I);

where the nitro group is substituted at any one of the available benzene positions 2–6; where R and A separately represent the groups $NO_2$, CN, $COOR^1$, $CONR^1R^2$, $CSNR^1R^2$ or $SO_2NR^1R^2$ and A is substituted at one of the available benzene positions 2–6; where B represents $N(CH_2CH_2halogen)_2$ or $N(CH_2CH_2OSO_2R^3)_2$ substituted at any one of the available benzene positions; and where $R^1$, $R^2$ and $R^3$ separately represent H, or lower alkyl optionally substituted with hydroxyl, ether, carboxyl or amino functions, including cyclic structures, or $R^1$ and $R^2$ together with the nitrogen form a heterocyclic structure.

Where $R^1$, $R^2$ and/or $R^3$ represent lower alkyl the group may contain from 1 to 6 carbon atoms.

Where $R^1$, $R^2$ and/or $R^3$ represent groups containing tertiary amines, the N-oxides of those tertiary amine moieties are also included.

The compounds of formula (I) have cytotoxic and antitumour activity and are useful as hypoxia-selective cytotoxins, reductively-activated prodrugs for cytotoxins, hypoxic cell radiosensitisers, and anticancer agents.

Some of the compounds of formula (I) form pharmaceutically-acceptable addition salts with both organic and inorganic acids, and these addition salts also form part of the present invention. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic and the like. Some of the compounds of formula (I) form pharmaceutically-acceptable addition salts with both organic and inorganic bases, and these addition salts also form part of the present invention. Examples of suitable bases for salt formation are sodium and potassium carbonate, sodium and potassium hydroxide, ammonia, triethylamine, triethanolamine and the like.

The compounds of formula (I) and the acid or base addition salts and the 1N-oxides thereof may be prepared by the processes outlined in the following Schemes 1 to 7.

Specific but non-limitative examples of the processes outlined in Schemes 1 to 7 are given hereinafter in Examples A to H respectively.

Scheme 1

Scheme 2

Scheme 3

The invention also relates to the preparation of compounds of the general formula I, the acid or base addition salts and the N-oxides thereof, by a process as outlined in any one of Schemes 1–7 above or by an obvious chemical equivalent thereof. The invention includes also those forms of the preparation processes according to which a compound obtainable as intermediate at any stage of the process is used as starting material and the remaining steps are carried out, or a starting material is used in the form of a derivative or salt or, especially, is formed under the reaction conditions.

The following Table 1 sets out physicochemical data for 24 compounds within the general formula (I), representative of it, and preparable by the processes of the invention.

TABLE 1

Analytical and physicochemical data for nitroaniline mustards of general formula 1.

| No. | A | $NO_2$ | B | R | mp (°C.) | formula | analyses[a] |
|---|---|---|---|---|---|---|---|
| 1 | 2-$NO_2$ | 4 | 5-N(CH$_2$CH$_2$Cl)$_2$ | $CONH_2$ | 109–111 | $C_{11}H_{12}Cl_2N_4O_5$ | C, H, N, Cl |
| 2 | 2-$NO_2$ | 4 | 5-N(CH$_2$CH$_2$Br)$_2$ | $CONH_2$ | 126–128 | $C_{11}H_{12}Br_2N_4O_5$ | C, H, N |
| 3 | 2-$NO_2$ | 4 | 5-N(CH$_2$CH$_2$I)$_2$ | $CONH_2$ | 170–172 | $C_{11}H_{12}I_2N_4O_5$ | C, H, N, I |

TABLE 1-continued

Analytical and physicochemical data for nitroaniline mustards of general formula 1.

| No. | A | NO$_2$ | B | R | mp (°C.) | formula | analyses[a] |
|---|---|---|---|---|---|---|---|
| 4 | 2-NO$_2$ | 4 | 5-N(CH$_2$CH$_2$OMs)$_2$[b] | CONH$_2$ | 142–144 | C$_{13}$H$_{18}$N$_4$O$_{11}$S$_2$ | C, H, N, S |
| 5 | 2-NO$_2$ | 4 | 5-N(CH$_2$CH$_2$Cl)$_2$ | COOMe | 136.5–138 | C$_{12}$H$_{13}$Cl$_2$N$_3$O$_6$ | C, H, N, Cl |
| 6 | 2-NO$_2$ | 4 | 5-N(CH$_2$CH$_2$Cl)$_2$ | COOH | 125–127 | C$_{11}$H$_{11}$Cl$_2$N$_3$O$_6$·½EtOAc | C, H, N |
| 7 | 2-NO$_2$ | 4 | 5-N(CH$_2$CH$_2$Cl)$_2$ | CN | 127 | C$_{11}$H$_{10}$Cl$_2$N$_4$O$_4$ | C, H, N |
| 8 | 2-NO$_2$ | 4 | 5-N(CH$_2$CH$_2$Cl)$_2$ | CONHMe | 180.5 | C$_{12}$H$_{14}$Cl$_2$N$_4$O$_4$ | C, H, N, Cl |
| 9 | 2-NO$_2$ | 4 | 5-N(CH$_2$CH$_2$Cl)$_2$ | CONMe$_2$ | 130.5 | C$_{13}$H$_{16}$Cl$_2$N$_4$O$_5$ | C, H, N |
| 10 | 2-NO$_2$ | 4 | 5-N(CH$_2$CH$_2$Cl)$_2$ | CONX[c] | 140–142 | C$_{15}$H$_{18}$Cl$_2$N$_4$O$_6$ | C, H, N |
| 11 | 2-NO$_2$ | 4 | 5-N(CH$_2$CH$_2$Cl)$_2$ | CONH(CH$_2$)$_2$NMe$_2$·HCl | 85–90 | C$_{15}$H$_{21}$Cl$_2$N$_5$O$_5$·HCl | C, H, N |
| 12 | 2-NO$_2$ | 4 | 5-N(CH$_2$CH$_2$Cl)$_2$ | CONH(CH$_2$)$_2$NX[c]·HCl | 119–120 | C$_{17}$H$_{23}$Cl$_2$N$_5$O$_6$·HCl | C, H, N, Cl |
| 13 | 2-NO$_2$ | 4 | 5-N(CH$_2$CH$_2$Cl)$_2$ | CSNH$_2$ | 166–167 | C$_{11}$H$_{12}$Cl$_2$N$_4$O$_4$S | C, H, N, Cl |
| 14 | 2-NO$_2$ | 4 | 5-N(CH$_2$CH$_2$Cl)$_2$ | CONH(CH$_2$)$_2$N(O)Me$_2$ | 165–169 | C$_{15}$H$_{21}$Cl$_2$N$_5$O$_6$·HCl | C, H, N, Cl |
| 15 | 2-NO$_2$ | 4 | 5-N(CH$_2$CH$_2$Cl)$_2$ | CONH(CH$_2$)$_2$COOH | 150–153 | C$_{14}$H$_{16}$Cl$_2$N$_4$O$_7$ | C, H, N |
| 16 | 2-NO$_2$ | 4 | 5-N(CH$_2$CH$_2$Cl)$_2$ | CONHCH$_2$CH$_2$OH | 157–158 | C$_{13}$H$_{16}$Cl$_2$N$_4$O$_6$ | C, H, N, Cl |
| 17 | 2-NO$_2$ | 4 | 5-N(CH$_2$CH$_2$Cl)$_2$ | CONHCH$_2$CH(OH)CH$_2$OH | gum | C$_{14}$H$_{18}$Cl$_2$N$_4$O$_7$ | C, H, N, Cl |
| 18 | 2-NO$_2$ | 4 | 5-N(CH$_2$CH$_2$Cl)$_2$ | SO$_2$NH$_2$ | 153–154 | C$_{10}$H$_{12}$Cl$_2$N$_4$O$_6$S | C, H, N, S |
| 19 | 3-NO$_2$ | 5 | 5-N(CH$_2$CH$_2$Cl)$_2$ | CONH$_2$ | 123–124 | C$_{11}$H$_{12}$Cl$_2$N$_4$O$_5$ | C, H, N, Cl |
| 20 | 3-NO$_2$ | 5 | 5-N(CH$_2$CH$_2$Cl)$_2$ | CONH(CH$_2$)$_2$NMe$_2$ | 115–118 | C$_{15}$H$_{21}$Cl$_2$N$_5$O$_5$ | C, H, N, Cl |
| 21 | 2-NO$_2$ | 6 | 5-N(CH$_2$CH$_2$Cl)$_2$ | CONH$_2$ | 141–141.5 | C$_{11}$H$_{12}$Cl$_2$N$_4$O$_5$ | C, H, N, Cl |
| 22 | 2-NO$_2$ | 6 | 5-N(CH$_2$CH$_2$Cl)$_2$ | CONH(CH$_2$)$_2$NMe$_2$·HCl | 180–182 | C$_{15}$H$_{21}$Cl$_2$N$_5$O$_5$·HCl | C, H, N, Cl |
| 23 | 3-NO$_2$ | 5 | 4-N(CH$_2$CH$_2$Cl)$_2$ | CONH$_2$ | 113–116 | C$_{11}$H$_{12}$Cl$_2$N$_4$O$_5$ | C, H, N, Cl |
| 24 | 3-NO$_2$ | 5 | 4-N(CH$_2$CH$_2$Cl)$_2$ | CONH(CH$_2$)$_2$NMe$_2$·HCl | 145–148 | C$_{15}$H$_{21}$Cl$_2$N$_5$O$_5$·HCl·H$_2$O | C, H, N |

Footnotes for Table 1
[a]Analyses for all listed elements within ± 0.4%.
[b]OMs = OSO$_2$CH$_3$.
[c]X = morpholide: (CH$_2$CH$_2$)$_2$O.

The following Examples A to H illustrate the preparation of compounds and representative of the general formula (I), and specifically the compounds listed in Table 1.

EXAMPLE A

Preparation of 5-[N,N'-bis(2-methanesulfonoxyethyl)amino]-2,4-dinitrobenzamide (4) (Ia: X=OSO$_2$Me; R=CONH$_2$) and analogues by the method outlined in Scheme 1.

Treatment of 5-chloro-2,4-dinitrobenzoic acid (II: Y=OH) [Goldstein, H.; Stamm. R. *Helv. Chim. Acta*, 1952,35, 133014 1332] with SOCl$_2$ followed by ammonia gave 5-chloro-2,4-dinitrobenzamide (II: Y=NH$_2$), mp 210 ° C. (dec)[Goldstein, H.; Stammm, R. *Helv. Chim. Acta*. 1952, 35, 1330–1332 report mp 212° C.]. $^1$H NMR (CD$_3$COCD$_3$) δ8.68 (s, 1 H, H-3), 8.02 (s, 1 H, H-6), 7.50 (br, 2 H, CONH$_2$). This amide was heated with diethanolamine in dioxan to give 5-[N,N-bis(2-hydroxyethyl)]amino-2,4-dinitrobenzanude (III) (45% yield), mp (EtOAc) 176°–178° C. $^1$H NMR (CD$_3$SOCD$_3$) δ8.47 (s, 1 H, ArH3), 8.07, 7.73 (2 br, 2 H, CONH$_2$), 7.35 (s, 1H, ArH6), 4.80 (m, 2H, OH), 3.83–3.20 (m, 8 H, CH$_2$N, CH$_2$O). Anal. (C$_{11}$H$_{14}$N$_4$O$_7$) C,H,N.

Methanesulfonyl chloride (5.17 ml, 0.067 mol) was added dropwise to a solution of the above amide diol (10.00 g, 0.032 mol) in dry pyridine (150 mL.) at 0° C. After a further 10 minutes at 0° C., the solution was stirred at 20° C. for 30 minutes, and then volatiles were removed under reduced pressure at below 40° C. The residue was partitioned between EtOAc and water, and the organic residue was chromatographed on silica gel. Elution with EtOAc gave foreruns, followed by 5-[N,N-bis(2-methanesulfonoxyethyl)amino]-2,4-dinitrobenzamide (4) (Ia: X=OSO$_2$Me; R=CONH$_2$) (11.05 g, 74%), mp (sealed tube: ex EtOAc/petroleum ether) 60° C. $^1$H NMR(CD$_3$COCD$_3$) δ8.54 (s, 1 H, H-3), 7.65 (s, 1 H, H-6), 4.49 (t, J=5.3 Hz, 4 H, CH$_2$OSO$_2$CH$_3$), 3.89 (t, J=5.3 Hz, 4 H, CH$_2$N), 3.09(s, 6H, SO$_2$CH$_3$), 2.90(br s, NH$_2$). $^{13}$C NMR δ167.01 (CONH$_2$), 148.56 (C-5), 140.45, 138.44 (C-2,4), 138.57 (C-1), 124.92, 123.06 (C-3,6), 67.65 (CH$_2$OSO$_2$CH$_3$), 52.02 (CH$_2$N), 37.23 (SO$_2$CH$_3$). Anal. (C$_{13}$H$_{18}$N$_4$O$_{11}$S$_2$) C,H,N,S.

The above dimesylate (4) (15.0 g, 31.9 mol) was dissolved in dry DMF (150 mL) The solution was treated with solid LiCl (20 g), warmed to 100° C. with vigorous stirring for 1h, and then concentrated to dryness. The residue was partitioned between EtOAc and water, and the organic portion was washed well with 3N HCl, worked up to give a waxy solid, and chromatographed on silica. Elution with EtOAc/petroleum ether (1:1) gave foreruns, while EtOAc/petroleum ether (3:2) gave 5-[N,N-bis(2-chloroethyl)amino]-2,4-diritrobenzamide (1) (Ia. X=Cl, R= CONH$_2$) (7.51 g, 67%)which crystallised from EtOAc/petroleum ether as small orange needles, m.p. 109°–111° C., $^1$H NMR (CD$_3$COCD$_3$)δ8.52 (s, 1H, H-3), 758 (s, 1H, H-6), 7.10 (br, 2H, CONH$_2$), 3.89–3.81 (m, 8H, NCH$_2$,CH$_2$,Cl). $^{13}$C NMR δ167.10 (CONH$_2$), 148.31 (C-5), 140.08 (C-2), 138.84 (C-1), 138.20 (C-4), 124.94, 122.24 (C-3,6), 54.25 (CH$_2$,N), 42.04 (CH$_2$Cl) $^M$/z 354,352,350 (M+, 2%), 303.301 (67, 24%),222(25),185(26),171(29),100(74),65(25),63(56),56 (57),36(100).Found M+354.0124; 352.0123; 350.0189. Anal. (C$_{11}$H$_{12}$Cl$_2$N$_4$O$_5$) C, H, N, I.

A solution of the above dimesylate (4) (1.00 g, 2.12 mmol) in dry DMF (50 mL) was treated with solid NaBr (10.0 g), warmed to 120° C. with vigorous stirring for 15 min, and then concentrated to. dryness under reduced pressure. The residue was partitioned between EtOAc and water, and the organic portion was washed well with 3N HCl and worked up. Chromatogaraphy of the residue on silica and elution with EtOAc/petroleum ether (1:1) gave 5-[N,N-bis (2-bromoethyl)amino]-2,4-dinitrobenzamide (2) (Ia: X=Br, R=CONH$_2$) (0.73 g, 78% yield), mp (EtOAc/petroleum ether) 126°–128° C. $^1$H NMR (CD$_3$COCD$_3$) δ8.53 (s, 1 H, H-3), 7.58 (s, 1H, H-6), 3.89 (t, J=6.6 Hz, 4 H, CH$_2$N), 3.73(t,J=6.6 Hz, 4H, CH$_2$Br), 2.93 (br, 2H, CONH$_2$), $^{13}$C NMR δ167.20 (CONH$_2$), 147.89 (C-5), 140.06, 138.26 (C-2,4), 138.75 (C-1), 124.95, 122.30 (C-3,6), 54.11 (CH$_2$N), 29.8 (CH$_2$Br). Anal.(C$_{11}$H$_{12}$Br$_2$N$_4$O$_5$) C,H,N.

A similar reaction using NaI gave 5-[N,N-bis(2-iodoethyl)amino]-2,4-dinitrobenzamide (3) (Ia: X=I, R=CONH$_2$) in 92% yield. mp (EtOAc/petroleum ether) 170°–172° C. $^1$H NMR (CD$_3$COCD$_3$) δ8.52 (s, 1 H, H-3), 7.55 (s, 1H, H-6), 3.84 (t, J=7.2 Hz, 4 H, CH$_2$N), 3.50 (t, J=7.2 Hz, 4 CH$_2$Br), 2.88 (br, 2H, CONH$_2$). $^{13}$C NMR δ167.09 (CONH$_2$), 147.17 (C-5), 140.08, 138.33 (C-2,4), 138.74 (C-1), 124.94, 122.31 (C-3,6), 54.89 (CH$_2$N), 1.72 (CH$_2$I). Anal. (C$_{11}$H$_{12}$I$_2$N$_4$O$_5$) C,H,N,I.

EXAMPLE B

Methyl 5-[N,N-bis(2-chloroethyl)amino]-2,4-dinitrobenzoate (5) (VI: X=Cl) and analogues by the method outlined in Scheme 2.

Methyl 5-chloro-2,4-dinitrobenzoate (IV) (1.24 g, 4.76 mmol) was treated with diethanolamine (1.00 g, 9.52 mmol) in dioxane (50 mL) at 50 ° C. for 3 h, and the residue after workup was chromatographed on silica gel. Elution with EtOAc gave methyl 5-[N,N-bis(2-hydroxyethyl)amino]-2,4-dinitrobenzoate (V) (1.52 g, 97%). mp (EtOAc/petroleum ether) 104°–106° C. $^1$H NMR (CDCl$_3$) δ8.48 (s, 1 H, H-3), 7.45 (s, 1H, H-6), 3.95 (s, 3H, OCH$_3$), 3.81 (t, J=5.0 Hz, 4 H, CH$_2$OH), 3.60 (t,J=5.0 Hz, 4H, CH$_2$N), 2.20 (br, 2H, OH). $^{13}$C NMR δ165.89 (COOMe), 147.53 (C-5), 138.67, 136.21 (C-2,4), 133.30 (C-1), 124.22, 121.65 (C-3,6), 59.34 (CH$_2$OH), 54.59 (CH$_2$N), 53.74 (OCH$_3$). Anal. (C$_{12}$H$_{15}$N$_3$O$_8$) C,H,N.

A solution of this diol (1.50 g, 4.56 mmol) and Et$_3$N (1.33 mL, 9.57 mmol) in dry CH$_2$Cl$_2$ (60 mL) was treated with MsCl (0.73 mL 9.34 mmol) at 0° C., and poured into saturated aqueous NaHCO$_3$ after 15 min. The crude dimesylate (VI: X=OSO$_2$Me) from workup was treated directly with excess LiCl in DMF at 120° C. for 30 min. The mixture was poured into brine, extracted with EtOAc, worked up, and chromatographed on silica gel. Elution with EtOAc/petroleum ether gave methyl 5-[N,N-bis(2-chloroethyl)amino]-2,4-dinitrobenzoate (5) (VI: X = Cl; Y$^1$=OMe) (1.34 g, 80%). mp (EtOAc/petroleum ether) 136.5°–138 ° C. $^1$H NMR (CDCl$_3$) δ8.54 (s, 1H, H-3), 7.34 (s, 1 H, H-6), 3.97 (s, 3 H, OCH$_3$), 3.68 (br s, 8 H, NCH$_2$CH$_2$Cl). $^{13}$C NMR δ165.30 (COOCH$_3$), 147.22 (C5), 139.81, 137.82 (C-2,4), 133.39 (C-1), 124.33, 121.77 (C-3,6), 53.86 (OCH$_3$), 53.78 (CH$_2$N), 40.69 (CH$_2$Cl). Anal. (C$_{12}$H$_{13}$Cl$_2$N$_3$O$_6$) C,H,N,Cl.

Hydrolysis of (5) with 4N KOH in p-dioxane at 20° C. for 15 min gave a quantitative yield of 5-[N,N-bis(2-chloroethyl)amino]-2,4-dinitrobenzoic acid (6) (Ib: X=Cl, R=COOH). mp (EtOAc/petroleum ether) 125°–127° C. $^1$H NMR (CD$_3$COCD$_3$) δ8.56 (s, 1H, H-3), 7.72 (s, 1H, H-6), 3.89–3.86 (br, 8 H, NCH$_2$CH$_2$Cl), 3.78 (br, COOH). $^{13}$C NMR δ166.02 (COOH), 148.52 (C-5), 140.25, 138.09 (C-2, 4), 134.72 (C-1), 124.87, 122.58 (C-3,6), 54.12 (CH$_2$N), 42.12 (CH$_2$Cl). Anal. (C$_{11}$H$_{11}$Cl$_2$N$_3$O$_6$/½EtOAc) C,H,N,Cl.

Treatment of (6) with excess SOCl$_2$ containing a drop of DMF under reflux for 20 min, followed by concentration to dryness and azeotroping with benzene, gave crude 5-[N,N-bis(2-chloroethyl)amino]-2,4-dinitrobenzoyl chloride (VI: X=Cl; Y$^1$=Cl). This was dissolved in Me$_2$CO (20 ML), cooled to 0° C., treated with excess 40% aqueous methylamine. The product was purified by chromatography on silica gel, elution with EtOAc/petroleum ether (1:1) giving N-methyl [N,N-bis(2-chloroethyl)amino]-2,4-dinitrobenzamide (8) (Ib: X=Cl, R=CONHMe). mp (EtOAc/petroleum ether) 180.5° C. $^1$H NMR (CD$_3$COCD$_3$) δ8.53 (s, 1 H., ArH3), 7.75 (br, 1 H, CONH), 7.56 (s, 1H, H-6), 3.88–3.80 (m, 8 H, N-CHCH$_2$CH$_2$Cl), 2.90, 2.89 (2s, 3H, CONHMe). $^{13}$NMR δ165.89 (CONH), 148.43 (C-5), 140.05, 138.26 (C-2,4), 138.94 (C-1), 125.05, 122.45 (C-3, 6), 54.20 (CH$_2$N), 42.10 (CH$_2$Cl), 26.69 (CONHCH$_3$). Anal. (C$_{12}$H$_{14}$Cl$_2$N$_4$O$_5$) C,H,N,Cl.

Similar treatment of the acid chloride (VI: X=Cl; Y$^1$=Cl) with ammonia or suitable amines gave:

5-[N,N-bis(2-chloroethyl)amino]-2,4-dinitrobenzamide (4) (Ib: X=Cl, R=CONH$_2$) (67% yield). mp (EtOAc/petroleum ether) 109°–111° C. $^1$H NMR (CD$_3$COCD$_3$) δ8.52 (s, 1H, H-3), 7.58 (s, 1 H, H-6), 7.10 (br, 2 H, CONH$_2$), 3.89–3.81 (m, 8H, NCH$_2$CH$_2$Cl). $^{13}$C NMR δ167.10 (CONH$_2$), 148.31 (C-5), 140.08 (C-2), 138.84 (C-1), 138.20 (C-4), 124.94, 122.24 (C-3,6), 54.25 (CH$_2$N), 42.04 (CH$_2$Cl). $^M$/z 354, 352, 350 (M$^{30}$, 2%), 303, 301 (67, 24%), 222 (25), 185 (26), 171(29), 100(74), 65(25), 63(56), 56(57), 36(100). Found M$^+$354.0124; 352.0123; 350.0189. C$_{11}$H$_{12}$Cl$_2$N$_4$O$_5$ requires 354.0126; 352.0155; 350.0185. Anal. (C$_{11}$H$_{12}$Cl$_2$N$_4$O$_5$) C,H,N,Cl.

N,N-dimethyl [N,N-bis(2-chloroethyl)amino]-2,4-dinitrobenzainide (9) (Ib: X=Cl, R=CONMe$_2$) (65% yield). mp (CHCl$_3$/petroleum ether) 130.5° C. $^1$H NMR (CDCl$_3$) δ8.61 (s, 1 H, H-3), 7.07 (s, 1 H, H-6), 3.62 (s, 8 H, NCH$_2$CH$_2$Cl), 3.07.2.78 (2×3H, CON(CH$_3$)$_2$)). $^{13}$C NMR δ166.12 (CON(CH$_3$)$_2$)), 148.33 (C-5), 138.88, 135.75 (C-2,4), 137.82 (C-1), 124.92, 120.00 (C-3,6), 53.55 (CH$_2$N), 40.98 (CH$_2$Cl), 38.06,34.85 (CON(CH$_3$)$_2$)). Anal. (C$_{13}$H$_{16}$Cl$_2$N$_4$O$_5$) C,H,N.

N-morpholino [N,N-bis(2-chloroethyl)amino]-2,4-dinitrobenzamiide (10) (Ib: X=Cl, R=CON(CH$_2$; CH$_2$)$_2$O), mp (CHCl$_3$/hexane) 140°–142° C. $^1$H NMR (CDCl$_3$) δ8.66 (s, 1H, ArH-3), 7.55 (s, 1 H, ArH-6), 3.68 (br, 10H, NC$\underline{H}_2$,C$\underline{H}_2$,Cl and C$\underline{H}_2$O ), 3.60 & 3.34 (2×m, 2×2 H, CH$_2$NCO). $^{13}$C NMR δ165.22 (CON), 149.34 (C-5), 139.88, 137.00 (C-2,4), 138.26 (C-1), 125.59, 121.17 (C-3,6), 66.92, 66.79 (CH$_2$O), 54.22 (CH$_2$N, 47.88, 42.80 (CONHC$\underline{H}_2$), 42.26 (CH$_2$Cl). Anal. (C$_{15}$H$_{18}$Cl$_2$N$_4$O$_6$) C,H,N.

N-[2-(dimethylamino)ethyl] [N,N-bis(2-chloroethyl)amino]-2,4-dinitrobenzamide (11) (Ib: X=Cl, R=CONHCH$_2$CH$_2$NMe$_2$). mp (hydrochloride salt from MeOH/EtOAc) 85°–90° C. $^1$H NMR (D$_2$O) δ8.76 (s, 1H, ArH-3), 7.59 (s, 1H, ArH-6), 3.86–3.80 (m, 10H, NC$\underline{H}_2$C$\underline{H}_2$Cl and C$\underline{H}_2$NH$^{+Me}$$_2$), 3.53 t, J=6.1 Hz, 2H, CONHC$\underline{H}_2$), 3.06 (s, 6H, NMe$_2$) $^{13}$C NMR δ170.77 (C$\underline{O}$NH), 166.12, 1451.39 (C-5), 140.53, 137.51 (C-2, 4), 138.18 (C-1), 128.25, 123.39 (C-3,6), 58.46 (C$\underline{H}_2$N$^+$HMe$_2$), 55.49 (CH$_2$N), 45.67 (N$^+$HMe$_2$), 43.97 (CH$_2$Cl), 38.54 (CONHC$\underline{H}_2$). Anal. (C$_{15}$H$_{21}$Cl$_2$N$_5$O$_5$.HCl) C,H,N.

A solution of the free base of (11) (0.50 g, 1.18 mmol) in CH$_2$Cl$_2$ (15 mL) was treated with a solution of 2-benzenesulfonyl-3—phenyloxaziridine [Davis, F.; Stringer, C.D. J. Org. Chem., 1982, 47, 1775–1777]. (0.32 g, 1.24 mmol) in CH$_2$Cl$_2$ (3 mL) was added dropwise to. After 10min, petroleum ether (10 mL) was added, the solution was cooled at −30° C. overnight, and the resulting solid was dried under high vacuum to give N-(N$^1$,N$^1$-dimethylaminoethyl) [N,N-bis(2-chloroethyl)amino]-2,4-dinitrobenzamide N$^1$-oxide (14) ((Ib: X=Cl, R=CONHCH$_2$, CH$_2$N(O)Me$_2$) as a hygroscopic foam. Treatment with MeOH/HCl gave the hydrochloride salt (0.36g, 64%). mp (MeOH/$^i$Pr$_2$O) 165°–169° C. $^1$H NMR (D$_2$O/(CD$_3$)$_2$SO) δ8.82 (s, 1H, H-3), 7.46 (s, 1H, H-6), 3.98, 3.93 (2xt, J=5.1 Hz, 2×2 H, CH$_2$CH$_2$), 3.82 (t, J=4.7 Hz, 4H, CH$_2$Cl), 3.77 (t, J=4.7 Hz, 4 H, CH$_2$N), 3.57 (s, 6 H, N(CH$_3$)$_2$). $^{13}$C NMR ($D_2O/(CD_3)_2SO$) δ170.71 (COHH), 151.63 (C-5), 140.68, 137.31 (C-3,6), 69.20 ($CH_2NOMe_2$), 59.03 ($NOMe_2$), 55.40 ($CH_2N$), 44.06 ($CH_2Cl$), 36.45 (CONH CH2). Anal. ($C_{15}H_{21}Cl_2N_5$·HCl) C,H,N,Cl.

N-[2-(morpholino)ethyl][N,N-bis(2-chloroethyl)amino]-2,4-dinitrobenzainide (12) (Ib: X=Cl,R= $CONHCH_2CH_2N(CH_2CH_2)_2O$) as a gum. The hydrochloride salt crystallized from MeOH/$^i$Pr$_2$O, mp 119°–120° C. $^1$H NMR ($D_2O$) δ8.81 (s, 1 H, H-3), 7.59 (s, 1 H, H-6), 4.07 (br, NH and HCl), 3.91 (t, J=6.0 Hz, 4 H, $N^{+CH}_2CH_2O$), 3.86–3.81 (m, 10 H, $NCH_2CH_2Cl$ and $CH_2CH_2N^+$), 3.56 (t, J=6.0 Hz, 6 H, $N^+CH_2O$ and $CONHCH_2$). $^{13}$C NMR δ171.17 (CONH), 151.69 (C-5), 140.61, 137.28 (C-2,4), 138.12 (C-1) 128.53, 123.48 (C-3,6), 66.30 ($N^+CH_3C_H_2O$),58.07 ($CH_2N^+$), 55.48 (CH2N), 54.65 ($N^{+CH}_2CH_2O$), 44.09 ($CH_2Cl$), 36.84 ($CONHCH_2$). Anal. ($C_{17}H_{23}Cl_2N_5O_5$·HCl·½$H_2O$) C,H,N,Cl.

N-(2-hydroxyethyl) 5-[N,N-bis(2-chloroethyl)amino]-2,4-dintrobenzamide (16)(Ib: X=Cl, R=$CONHCH_2CH_2OH$) (1.24 g, 85%), mp (EtOAc/petroleum ether) 157°–158° C. $^1$H NMR (($CD_3)_2SO$) δ8.73 t,J=5.5 Hz, 1 H, CONH), 8.53 (s, 1 H, H-3), 7.45 (s, 1 H, H-6), 4.76 (t, J=5.5 Hz, 1 H, OH), 3.82 (t, J=6.0 Hz, 4 H, $CH_2Cl$), 3.68 (t, J=6.0 Hz, 4 H, $CH_2N$), 3.54 (dt, J=6.1, 5.5 Hz, 2 H, $CH_2OH$), 3.31 (dt, J=6.1, 5.5 Hz, 2 H, $CONHCH_2$). $^{13}$C NMR (($CD_3)SO$) δ164.44 (CONH), 147.11 (C-5), 137. 87,136.27 (C-2,4), 137.32 (C-1), 124.24, 121.01 (C-3,6), 59.32 ($CH_2OH$), 52.44 ($CH_2N$), 41.93 ($CONHCH_2$), 41.65 ($CH_2Cl$). Anal. ($C_{13}H_{16}Cl_2 N_2O_6$) C,H,N,Cl.

N-(2,3-dihydroxypropyl)5-[N,N-bis(2-chloroethyl)amino]-2,4-dinitrobenzarnide(17) (Ib: X=Cl, R=$CONHCH_2CH(OH)CH_2OH$) (0.96 g, 59%) as a hygroscopic yellow foam. $^1$H NMR (($CD_3)_2SO$) δ8.70 (t,J 5.7 Hz, 1 H, CONH), 8.53 (s, 1 H, H-3), 7.44 (s, 1 H, H-6), 4.83 (d, J=4.9 Hz, 1 H, CHOH) 4.56 (t, J=5.7 Hz, 1 H, $CH_2OH$), 3.83 (t,J=5.9 Hz, 4 H, $CH_2Cl$), 3.68 (t,J=5.9 Hz, 4 H, $CH_2N$), 3.50–3.06 (m, 5 H, CONH $CH_2CHOHCH_2OH$). $^{13}$C NMR (($CD_3)_2SO$) δ164.61 (CONH), 147.12 (C-5), 37.94, 136.40 (C-2,4), 137.40 (C-1), 124.29, 121.18 (C-3,6), 70.08 (CHOH), 63.77 ($CH_2OH$), 52.55 ($CH_2N$), 42.79 ($CONHCH_2$), 41.72, ($CH_2Cl$). Anal. ($C_{14}H_{18}Cl_2N_4O_7$) C,H,N,Cl.

crude N-(2-methoxycarbonylethyl) 5-[N,N-bis(2-chloroethyl)amino]-2,4-dinitrobenzarnide [from treatment with β-alanine methyl ester hydrochloride] (Ib: X=Cl, R=$CONHCH_2CH_2COOMe$) as a yellow oil. This was immediately dissolved in THF (25 mL) and treated with aqueous KOH (10 mL of 2N) at 20° C. for 3h. The solution was then acidified with conc. HCl, extracted with EtOAc, and worked up as usual. Chromatography on silica, eluting with EtOAc, gave N-(2-carboxyethyl) 5-[N,N-bis(2-chloroethyl)amino]-2,4-dinitrobenzamide (15) (Ib: X=Cl, R=$CONHCH_2CH_2COOH$) (0.72 g, 68%), mp (EtOAc/petroleum ether) 150°–153° C. $^1$H NMR (($CD_3)_2SO$) δ12.27 (br, 1 H, COOH) 8.79 (t,J=5.6 Hz, 1 H, CONH), 8.54 (s, 1 H, H-3), 7.42 (s, 1 H, H-6) 3.83 (t,J=6.0 Hz, 2 H, $CH_2Cl$), 3.68 (t,J=6.0 Hz, 4 H, $CH_2N$), 3.44 (dxt, J=6.9, 2 H, 5.6 Hz, $CONHCH_2$), 2.53 (t, J=6.9 Hz, 2 H, $CH_2$, COOH). $^{13}$C NMR (($CD_3)_2SO$) δ172.74 (COOH), 164.53 (CONH), 147.21 (C-5), 137.94, 136.13 (C-2,4), 137.29 (C-1), 124.37, 120.93 (C-3,6), 52.58 ($CH_2N$), 41.72 ($CH_2Cl$), 35.24, 33.19 ($CONHCH_2CH_2$). Anal. ($C_{14}H_{16}Cl_2N_4O_7$) C,H,N,Cl.

EXAMPLE C

Preparation of 5-[N,N-bis(2-chloroethyl)aminol]-2,4-dinitrobenzonitrile (7) (Ic: X=Cl, R=CN) and 5-[NN-bis(2-chloroethyl)amino]-2,4-dinitrothiobenzamide (13)(Ic: X=Cl, R=$CSNH2$) by the method outlined in Scheme 3.

A solution of 5-[N,N-bis(2-chloroethyl)amino]-2,4-dinitrobenzanide (1) (VII) (0.20 g, 0.57 mmol) in $SOCl_2$ (5 mL) was heated under reflux in $N_2$ for 84 h. Excess $SOCl_2$ was removed under reduced pressure, and the residue was chromatographed on silica gel. Elution with EtOAc/petroleum ether (3:7) gave 5-[N,N-bis(2-chloroethyl)aminol]-2,4-dinitrobenzonitrile (7)(Ic: X=Cl, R=CN)(0.16 g, 87%), mp ($CHCl_3$) 127° C. $^1$H NMR ($CD_3COCD_3$) δ8.79 (s, 1 H, H-3), 8.19 (s, 1 H, H-6),3.93 (s, 8 H, $NCH_2CH_2Cl$). $^{13}$C NMR δ148.55 (C-5), 140.98, 139.07 (C-2, 4), 129.50, 126.10 (C-3,6), 115.05 (C-1), 112.84 (CN), 54.18 ($CH_2N$), 42.20 ($CH_2Cl$). Anal. ($C_{11}H_{10}$ $_{Cl2}N_4O_4$) C,H,N.

A solution of (1) (VII) (0.50 g, 1.42 mmol) in p-dioxane (20 mL) was treated with $P_2S_5$(0.63 g, 2.84 mmol) and $NaHCO_3$(0.24 g, 2.84 mmol) was heated under reflux with stirring for 3 h. The residue after workup was chromatographed on silica gel, and elution with EtOAc/petroleum ether (1:4) gave 5-[N,N-bis(2-chloroethyl)amino]-2,4-dinitrothiobenzamide (13) Ic: X=Cl, R=$CSNH_2$) (0.48 g, 92%), mp (EtOAc/petroleum ether) 166°–167° C. $^1$H NMR ($CD_3SOCD_3$) δ9.50, 9.34 (2xbr, 2 H, $CSNH_2$), 8.50 (s, 1 H, H-3), 7.45 (s, 1 H, H-6), 3.87, 3.82 (2xm, S H, $NCH_2CH_2Cl$). $^{13}$C NMR δ199.46 (CS), 148.08 (C-5), 143.87 (C-1), 139.51, 136.99 (C-2,4), 125.23, 121.36 (C-3, 6), 54.23 ($CH_2N$), 42.02 ($CH_2Cl$). Anal. ($C_{11}H_{12}Cl_2N_4O_4S$) C,H,N,S.

EXAMPLE D

Preparation of 5-[N,N-bis(2-chloroethyl)amino]-2,4-dinitrobenzenesulfonamide (18)(Id: X=Cl, R= $SO_2NH2$) by the method outlined in Scheme 4.

A solution of 5-chloro-2,4-dinitrobenzenesulfonamide (VIII) [Herbert, R.B. and Hollman, R.G. Tetrahedron, 1965, 21, 663–675] (1.55 g, 5.5 mmol) and diethanolarnine (1.16 g, 11 mmol) in dioxan (100 mL) was held at 60 ° C. for 1.5 h, then adsorbed directly onto silica gel. Excess solvent was evaporated under reduced pressure, and the residue was chromatographed on silica gel, eluting with EtOAc/MeOH (19:1), to give 5-[N,N-bis(2-hydroxyethyl)amino]-2,-dinitrobenzenesulfonamide (IX) (1.91 g, 99%), mp (EtOAc/petroleum ether) 138°–139° C. $^1$H NMR (($CD_3)_2SO$) δ8.53 (s, 1 H, H-3), 7.97 (s, 1 H, H-6), 7.93 (br s, 2 H, $SO_2NH_2$), 4.88 (t,J=5.1 Hz, 2 H, OH), 3.65 (dt,J=5.2, 5.1 Hz, 4 H, $CH_2OH$), 3.49 (t, J=5.1 Hz, 4 H, $NCH_2$). $^{13}$C NMR δ146.84 (C-5), 140.53 (C-1), 136.84, 134.39 (C-2,4), 125.70 (C-3), 54.27 ($NCH_3$). Anal. ($C_{10}H_{14}N_4O_8S$) C,H,N.

A stirred solution of the above diol (IX) (1.90 g, 5.43 mmol) and $Et_3N$ (1.90 mL, 14 mmol) in dry THF (60 mL) was treated dropwise at 0° C. with methanesulfonyl chloride (0.89 mL, 11 mmol). After a further 15 min, the solution was diluted with EtOAc, washed well with water, and worked up to give the crude dimesylate (Id: X=$OSO_2Me$, R=$SO_2NH_2$). This was immediately dissolved in DMF (50 mL) containing LiCl (20 g), and the mixture stirred at 130° C. for 15 min before solvent was removed under reduced pressure. The residue was partitioned between EtOAc and water, and the organic layer was worked up and chromatographed on silica gel. Elution with EtOAc gave 5-[N,N-bis(2-chloroethyl)

amino]-2,4-dinitrobenzenesulfonamide (18) (Id: X=Cl, R=SO$_2$NH$_2$) (1.47 g, 64%), mp 153°–154° C. (EtOAc/ petroleum ether). $^1$H NMR ((CD$_3$)$_2$CO) δ8.54, (S, 1H, H-3), 7.99 (br, 2H, SO$_2$NH$_2$), 7.91 (S, 1H, H-6), 3.84 (t, J=5.6 Hz, 4H, CH$_2$Cl), 3.67 (t, J=5.6 Hz, 4H, CH$_2$N). $^{13}$C NMR ((CD$_3$)$_2$CO) δ146.13 (C-5), 140.64 (C-1), 138.86, 136.93 (C-2,4), 124.95, 121.77 (C-3,6), 52.47 (CH$_2$N), 41.62 (CH$_2$Cl). Anal. (C$_{10}$H$_{12}$Cl$_2$N$_4$O$_6$S) C,H,N,S.

EXAMPLE E

Preparation of 2-[N,N-bis(2-chloroethyl)amino]-3,5-dinitrobenzamide (19) (Ie: R=CONH$_2$) and N-(N, N-dimethylaminoethyl) 2-[N,N-bis(2-chloroethyl) amino]-3,5-dinitrobenzamide (20) (Ie: R= CONHCH$_2$CH$_2$NMe$_2$) by the method outlined in Scheme 5.

Reaction of commercially-available 2-chloro-3,5-dinitrobenzoic acid (X) with SOCl$_2$ gave 2-chloro-3,5-dinitrobenzoyl chloride (XI: Z=Cl), which was quenched with ammonia to give 2-chloro-3,5-dinitrobenzamide (XI: Z=NH$_2$). A solution of this amide (1.00 g, 4.07 mmol) and Et$_3$N (1.42 g, 10 mmol) in p-dioxane (30 mL) was 0356 treated with N,N-bis(2-chloroethyl)amine hydrochloride (1.45 g, 8.14 mmol) at 50° C. for 18 h. The mixture was then poured into water and extracted with EtOAc to give an oil, which was chromatographed on silica gel. Elution with EtOAc/petroleum ether (1:1) gave 2-[N,N-bis(2-chloroethyl)amino]-3,5-dinitrobenzramide (19) (Ie: R=CONH$_2$) (1.15 g, 80%), mp (CHCl$_3$/petroleum ether) 123°–124° C. $^1$H NMR (CD$_3$SOCD$_3$) δ8.70 (d, J=2.7 Hz, 1 H, H-4), 8.49 (d, J=2.7 Hz, 1 H, H-6), 7.68, 7.35 (2xbr, 2H, CONH$_2$), 3.80, 3.61 (2,xt, J=6.9 Hz, y 8H, NCH$_2$CU$_2$Cl). 13C NMR δ167.94 (CONH$_2$), 147.27 (C-2), 147.2 0. 142.84 (C-3,5), 137.70 (C-1), 128.40, 123.24 (C-4:6), 55.84 (CH$_2$N), 42.28 ) (CH$_2$Cl). Anal. (C$_{11}$H$_{12}$Cl$_2$N$_4$O$_5$) C,H,N, Cl.

Similar treatment of the acid chloride (XI: Z=Cl) with N,N-dimethylaminoethyl in water at 0° C. gave N-(N,N-dimethylaminoethyl) 2-chloro-3,5-dinitrobenzamide (XI, Z=NTHCH$_2$CH$_2$NMe$_2$) as a viscous oil (5.6 g, 59%. The hydrochloride salt crystallised from MeOH/isopropyl ether, mp 220°–222° C. $^1$H NMR (D$_2$O) δ8.99 (d, J=2.3 Hz, 1H, ArH4), 8.74 (d, J=2.3 Hz, 1H, ArH6), 3.89 (t, J=6.3 Hz, 2H, CH$_2$N$^+$Me$_2$), 3.51 (t, J=6.3 Hz, 2H, CONHC$\underline{H}_2$), 3.04 (s, 6H, NMe$_2$). $^{13}$C NMR 169.32 (CONH), 150.88 (C-2), 148.70, 141.02 (C-3,5), 133.23 (C-1), 129.45, 125.27 (C-4, 6), 58.64 (C̲H$_2$N$^{+Me}$$_2$), 45.88 (N$^+$Me$_2$), 37.94 (CONH C̲H$_2$). Anal. (C$_{11}$H$_{13}$ClN$_4$O$_5$.HCl) C,H,N,Cl.

Reaction of this amide (XI: Z=NHCH$_2$CH$_2$CH$_2$NMe$_2$) with bis(2-chloroethyl)amine hydrochloride and Et$_3$N as above, followed by chromatography on silica gel and elution with EtOAc/MeOH (9:1) gave N-(N,N-dimethylaminoethyl) 2-[N,N-bis(2-chloroethyl)amino]-3,5-dinitrobenzamide (20) (Ie: R=CONHCH$_2$CH$_2$NMe$_2$), mp (EtOAc/petroleum ether) 115°–118° C. $^1$H NMR (CDCl$_3$) δ8.63 (s, 2H, ArH4), 7.41 (br, 1H, CONH), 3.74 (t, J=6.3 Hz, 4H, CH$_2$Cl), 3.59 (t, J=5.8 Hz, 2H, CONHC$\underline{H}_2$), 3.55 (t, J=6.3 Hz, 4H, NC$\underline{H}_2$CH$_2$Cl), 2.56 (t, J=5.8 Hz, 2H, CH$_2$NMe$_2$), 2.27 (s, 6H, NMe$_2$). $^{13}$C NMR 164.70 (CO), 145.93 (C-2), 144.86, 141.94 (C-3,5), 135.68 (C-1), 129.63 (C4), 123.16 (C-6), 57.51 (CONHC̲H$_2$), 54.82 (N C̲H$_2$CH$_2$Cl), 45.12 (NMe$_2$), 41.39 (NCH$_{2C\underline{H}2}$Cl), 37.67 (CONHC̲H$_2$). Anal. (C$_{15}$H$_{21}$Cl$_2$N$_5$O$_5$) C,H,N,Cl. (The hydrochloride salt was too hygroscopic to handle).

EXAMPLE F

Preparation of 3-[N,N-bis(2-chloroethyl)amino]-2,6-dinitrobenzamide (21) (If: R=CONH$_2$) and N-(N,N-dimethylaminoethyl) 3-[N,N-bis-(2-chloroethyl) amino]-2,6-dinitrobenzamide (22) (If: R= CONHCH$_2$CH2NMe$_2$) by the method outlined in Scheme 6.

A solution of 3-chlorobenzoic acid (60 g, 0.38 mol) in c.H$_2$SO$_4$ (600 ml) was treated portionwise with fuming nitric acid (d 1.42) (150 ml), and the solution was warmed gradually with stirring to 140° C. in an open flask, and held at this temperature for 6h. After cooling overnight, ice-water was added cautiously, and after chilling to 5° C. for 3h the precipitated product was removed by filtration and washed well with water. Crystallisation from aqueous EtOH gave 5-chloro-2,4-dinitrobenzoic acid (II: Y=OH) (62 g, 66%) mp 180°–183° C. [Goldstein, H.; Stamm, R. Helv. Chim. Acta, 1952, 35, 1330–1332 report mp 182°–183° C.]. The original filtrate and washings were combined and allowed to stand for several hours, depositing crystals of pure 3-chloro-2,6-dinitrobenzoic acid (XII) (8.4 g, 9%), mp (H$_2$O) 162°–163.5° C. $^1$H NMR (CD$_3$SOCD$_3$) δ10.50 (br, 1 H, COOH), 8.82 (d, J=8.8 Hz, 1 H, H-5), 8.62 (d, J=8.8 Hz, 1 H, H4). $^{13}$C NMR δ162.03 (COOH), 146.34 (C-2), 145.57 (C-6), 133.69 (C-5), 130.01 (C-1), 128.26 (C4), 125.19 (C-3). Anal. (C$_7$H$_3$ClN$_2$O$_6$) C,H,N,Cl.

The 3-chloro-2,6-dinitrobenzoic acid (XI) was converted to the ethyl ester, which was reacted as above with diethanolamine to give crude ethyl 3-[N,N-bis-(2-hydroxyethyl) amino]-2,6-dinitrobenzoate (XIII: X=OH, Z=OEt). Reaction of this with MsCl/LiCl gave ethyl 3-[N,N-bis(2-chloroethyl) amino]-2,6-dinitrobenzoate (XII: X=Cl, Z=OEt), mp (EtOAc/petroleum ether) 84°–87° C. $^1$H NMR (CD$_3$COCD$_3$) δ8.32 (d, J=9.4 Hz, 1H, H-5), 7.79 (d, J=9.4 Hz, 1H, H4) 4.39 (q, J=7.1 Hz, 2H, OCH$_2$CH$_3$), 3.85–3.77 (m, 8H, NCH$_2$CH$_2$Cl), 1.34 (t, J=7.1 Hz, 3H, OCH$_2$CH$_3$). $^{13}$C NMR δ163.24 (COOEt), 148.30 (C-3), 141.04, 138.80 (C-2,6), 128.84, 124.65 (CA,4.5), 127.39 (C-1), 63.94 (OCH$_2$CH$_3$), 54.39 (NCH$_2$), 42.00 (CH$_2$Cl) 13.89 (OCH$_2$CH$_3$). Anal. (C$_{13}$H$_{15}$Cl$_2$N$_3$O$_6$) C,H,N,Cl.

An X-ray crystallographic determination was carried out on this compound to confirm the structure.

Hydrolysis of this ester (XII: X=Cl, Z=OEt) in aqueous KOH/p-dioxane (30 mL) at 20° C. for 18h gave 3-[N,N-bis (2-chloroethyl)amino]-2,6-dinitrobenzoic acid (XIII: X=Cl, Z=OH), which was converted to the corresponding acid chloride (XIII: X=Cl, Z=Cl). A solution of this in Me$_2$CO at 0° C. was treated with excess aqueous ammonia, and the product was chromatographed on silica gel, EtOAc/ petroleum ether (1:1) eluting 3-[N,N-bis(2-chloroethyl) amino]-2,6-dinitrobenzamide (21) (If: R=CONH$_2$) (0.93 g), mp (EtOAc/petroleum ether) 140°–141.5° C. $^1$H NMR (CD$_3$COCD$_3$) δ8.26 (d, J=9.3 Hz, 1H, H-5), 7.71 (d, J=9.3 Hz, 1H, H-4), 7.63, 7.23 (2xbr, 2H, CONH$_2$), 3.75 (s, 8H, NCH$_2$CH$_2$Cl). $^{13}$C NMR δ163.99 (CONH$_2$), 147.38 (C-3), 142.92, 139.76 (C-2,6), 130.48 (C-1), 128.22, 124.23 (C4, 5), 54.74 (NCH$_2$), 42.00 (CH$_2$Cl). Anal. (C$_{11}$H$_{12}$Cl$_2$N$_4$O$_5$) C,H,N,Cl Similar treatment of the acid chloride (XIII: X=Cl, Z=Cl) with N,N-dimethylethylenediamine gave N-(N,N-dimethylaminoethyl) 3-[N,N-bis(2-chloroethyl)amino]-2,6-dinitrobenzamide (22) (If: R=CONHCH$_2$CH$_2$NMe$_2$). The hydrochloride salt crystallised from MeOH/isopropyl ether, mp 180°–182 ° C. 1H NMR (D$_2$O) δ8.37 (d, J=9.6 Hz, 1H, ArH5), 7.63 (d, J=9.6 Hz, 1H, ArH4), 3.80–3.71 (m, 10H, NCH$_2$CH$_2$Cl and CH$_2$NMe$_2$), 3.44 (t, J=6.4 Hz, 2H, CONHCH$_2$), 3.00 (s, 6H, NMe$_2$) $^{13}$C NMR δ168.75 (CONH), 150.91 (C-3), 141.55, 138.72 (C-2,6), 131.61 (C-4), 130.45 (C-1), 125.85 (C-5), 58.31 (CH$_2$N$^{30}$ Me$_2$), 55.74 (NCH$_2$CH$_2$Cl), 45.97 (N$^{30}$ Me$_2$), 44.16 (NCH2 CH$_2$Cl ), 37.91 (CONHCH$_2$). Anal. (C$_{15}$H$_{21}$Cl$_2$N5O$_5$. HCl) C,H,N,Cl.

EXAMPLE G:

Preparation of 4-[N,N-bis(2-chloroethyl)amino]-3,5-dinitrobenzamide (23) (Ig: X=Cl, R=CONH$_2$) and N-(N,N-dimethylaminoethyl) 4-[N,N-bis(2-chloroethyl)amino]-3,5-dinitrobenzamide (24) (Ig: X=Cl, R=CONHCH$_2$CH2NMe$_2$) by the method outlined in Scheme 7.

A solution of methyl 4-chloro-3,5-dinitrobenzoate (XIV) (10.0 g, 0.036 mol) and diethanolamine (7.66 g, 0.073 mol) in ρ-dioxane (60 mL) was stirred at 50° C. for 5h. Volatiles were removed under reduced pressure, and the residue was adsorbed directly onto silica gel and chromatographed. Elution with EtOAc/petroleum ether (1:10) gave foreruns, and subsequent elution with EtOAc/petroleum ether (3:2) gave methyl 4-[N,N-bis(2-hydroxyethyl)amino]-3,5-dinitrobenzoate (XV: X=OH, Z=OMe) (9.61 g, 80%), mp (CHCl$_3$/petroleum ether) 101°–103° C. $^1$H NMR (CDCl$_3$) δ8.52 (s, 2H, ArH-2,6), 3.97 (s, 3 H, COOCH$_3$), 3.76 (dxt, J=6.5, 4.7 Hz, 4H, CH$_2$OH), 3.26 (t, J=4.7 Hz, 4H, NCH$_2$), 2.76 (t, J=6.5 Hz, 2 H, OH). $^{13}$C NMR δ163.14 (COOCH$_3$), 145.50 (C-4), 142.54 (C-3,5), 131.19 (C-2,6), 123.59 (C-1), 59.16 (CH$_2$OH)1, 54.58 (CH$_2$N), 53.14 (OCH$_3$). Anal. (Cl$_{12}$H$_{15}$N$_3$O$_8$) C,H,N.

MsCl (3.93 mL, 0.049 mol) was added dropwise at 0 ° C. to a solution of the above diol (XV: X=OH, Z=OMe) (7.30 g, 0.022 mol) and Et$_3$N (7.72 mL, 0.055 mol) in CH$_2$C$_2$Cl$_2$ (100 mL). After 15 min, the solution was washed several times with water and worked up to give the crude dimesylate, which was treated with LiCl in DMF at 120 ° C. for 5 min. Workup and chromatography on silica gel (elution with EtOAc/petroleum ether (1:4)) gave methyl 4-[N,N-bis(2-chloroethyl)amino]-3,5-dinitrobenzoate (XV: X=Cl, Z=OMe) (6.21 g, 77%), mp (CHCl$_3$/petroleum ether) 93°–95° C. $^1$NMR (CDCl$_3$) δ8.54 (s, 2 H, H-2,6), 3.99H (s, 3H, COOCH$_3$), 3.63 (t, J=6.9 Hz, 4H, CH$_2$Cl), 3.43 (t, J=6.9 Hz, 4H, CH$_2$N). $^{13}$C NMR δ162.90 (COOCH$_3$), 147.83 (C4), 140.53 (C-3,5), 129.85 (C-2,6), 126.70 (C-1), 55.47 (CH$_2$N), 53.23 (OCH$_3$), 41.18 (CH$_2$Cl). Anal. (C$_{12}$H$_{13}$Cl$_2$N$_3$O$_6$) C,H,N,Cl.

Hydrolysis of this ester (XV: X=Cl,Z=OMe) with aqueous KOH/ρ-dioxane at 20° C. for 3h gave a quantitative yield of 4-[N,N-bis(2-chloroethyl)amino]-3,5-dinitrobenzoic acid (XV: X=Cl, Z=OH), mp EtOAc/petroleum ether) 164°–166° C. $^1$NMR ((CD$_3$)$_2$SO) δ8.61 (s, 2H, H-2,6), 3.78 (t, J=6.9 Hz, 4H, CH$_2$Cl), 3.52 (t, J=6.9 Hz, 4H, CH$_2$N) (COOH not visible). $^{13}$C NMR δ164.12 (COOH), 149.12 (C-4), 141.40 (C-3,5), 130.70 (C-2,6), 128.19 (C-1), 56.14 (CH$_2$N), 42.46 (CH$_2$Cl). Anal (C$_{11}$H$_{11}$Cl$_2$N$_3$O$_6$) C,H,N,Cl.

The above acid (XV: X=Cl, Z=OH) was converted to the crude acid chloride (XV: X=Cl, Z=Cl), which was dissolved in dry Et$_2$O (100 mL), cooled to 5° C., and treated dropwise with aqueous NH$_3$ (20 mL of a 3N solution, 60 mmol). After 10 min the solution was worked up, and the residue was chromatographed on silica. Elution with EtOAc/petroleum ether (3:7) gave foreruns, while EtOAc/petroleum ether (7:3) gave 4-[N,N-bis(2-chloroethyl)amino]-3,5-dinitrobeazamide ( 23) (Ig: X=Cl, R=CONH$_2$) (80% overall yield), mp (EtOAc/petroleum ether) 113°–116 ° C. $^1$H NMR (CD$_3$COCD$_3$) δ8.61 (s, 2 H, H-2,6), 7.98, 7.24 (2xbr, 2H, CONH$_2$), 3.75 (t, J=7.0 Hz, 4H, CH$_2$Cl), 3.50 (t, 4 H, CH$_2$N). $^{13}$C NMR δ164.91 (CONH$_2$), 149.32 (C-4), 140.07 (C-3,5), 132.18 (C-1), 128.91 (C-2,6), 56.37 (CH$_2$N), 42.55 (CH$_2$Cl). Anal. (C$_{11}$H$_{12}$Cl$_2$N$_4$O$_5$) C,H,N,Cl.

Similar treatment of the crude acid chloride (XV: X=Cl, Z=Cl) with N,N-dimethylethylenediamine gave N-(N,N-dimethylaminoethyl) 4-[N,N-bis(2-chloroethyl)amino]-3,5-dinitrobenzamide (24) (Ig: X=Cl, R=CONHCH$_2$CH$_2$NMe$_2$). The hydrochloride salt crystallised from MeOH/isopropyl ether, mp 145°–148° C. $^1$NMR (CD$_3$SOCD$_3$) δ10.65 (br, 1H, HCl), 9.49 (t, J=5.4 Hz, 1H, CONH), 8.75 (s, 2H, ArH2,6), 3.71 (t, J=6.9 Hz, 4H, NCH$_2$CH$_2$Cl ), 3.44–3.28 (m, 8H, NCH$_2$CH$_2$Cl and CH$_2$CH$_2$N$^+$Me$_2$), 2.83 (s, 6H, N$^+$Me$_2$). $^{13}$C NMR δ162.63 (CO), 147.43 (C-3,5), 138.75 (C-4), 130.22 (C-1), 128.31 (C-2,6), 55.44 (CH$_2$N$^+$Me$_2$), 54.75 (NCH$_2$CH$_2$Cl), 42.22 (N$^+$Me$_2$), 42.18 (NCH$_2$ CH$_2$Cl), 34.75 (CONHCH$_2$). Anal. (C$_{15}$H$_{21}$Cl$_2$N$_5$O$_5$.HCl) C,H,N,Cl.

The following Table 2 gives biological data for selected examples of the compounds listed in Table 1. The abbreviations used in Table 2 are:

No.
The number given the corresponding compound in Table 1.

IC$_{50}$
Growth inhibition studies were performed as described in detail elsewhere (W.R. Wilson, R.F. Anderson and W.A Denny. *J Med. Chem.*, 1989, 32, 23; G.J. Finlay, B.C. Baguley and W.R. Wilson. *Anal Biochem.*, 1984, 139, 172.), using 200 viable AA8 or 300 viable UV4 cells plus 5000 lethally-irradiated AA8 feeder cells per well in 96-well tissue culture dishes. AA8 and UV4 cells were maintained in logarithmic-phase growth in 25 cm$^3$ tissue culture flasks with subculture twice weekly by trypsinization. The growth medium was antibiotic-free α-MEM with 10% v/v heat-inactivated (560° C., 40 min) fetal calf serum. Doubling times were approximately 14h for AA8 and 15h for UV4 cells. Cultures were tested for mycoplasma contamination frequently, using, a cytochemical staining method (I.R. Chen, *Exp. Cell Res.*, 1977, 104, 255. Drugs were added 24 hours after initiating cultures in 96-well dishes, and cells were incubated under aerobic or hypoxic conditions for 18 hours before washing with fresh medium. The IC$_{50}$ was determined as the drug concentration needed to reduce the cell mass (protein content, measured after 72–78h by staining with methylene blue and measuring absorbance in a microplate photometer) to 50% of the mean value for 8 control cultures on the same 96-well plate.

HF$_{air}$
Ratio of IC$_{50}$ values for a compound after exposure as detailed above against AA8 and UV4 cell lines (HF=IC$_{50}$ (AA8)/IC$_{50}$(UV4)).

CT$_{10}$
The product (in μM-hr) of the drug concentration times the exposure time to reduce cell survival to 10% of control values in the clonogenic assay.

air/N$_2$
Ratio of CT$_{10}$ values after exposure of UV4 cells as detailed above under either aerobic (air) or hypoxic (N$_2$) conditions (=aerobic CT$_{10}$/hypoxic CT$_{10}$).

HF$_{NR-2}$
Ratio of IC$_{50}$ values for a compound after exposure as detailed above against the UV4 cell line in the presence and absence of the *E. coli* nitroreductase enzyme NTR-2.

TABLE 2

Biological activity of selected compounds of Table I

| No | $IC_{50}$ (AA8) (air: μM) | HF (air) | $CT_{10}$ (UV4) (air: μM-h) | $CT_{10}$ ratio (air/$N_2$) | $IC_{50}$ (UV4) (air: μM) | HF (NR-2) (air) |
|---|---|---|---|---|---|---|
| 1 | 468 | 6.8 | 2925 | 58 | 109 | 73.5 |
| 2 | 57 | 7.5 | 160 | 20 | 10.9 | 32.3 |
| 3 | 34 | 2.6 | 170 | 42 | 15 | 73.8 |
| 4 | >200 | — | 1200 | 17 | 99 | 10.0 |
| 6 | 10600 | 1.5 | >30000 | >2 | 317 | 0.76 |
| 7 | 24 | 6.8 | 86 | 8.5 | 2.3 | 9.2 |
| 8 | >100 | — | >360 | — | | |
| 9 | 310 | 1.4 | >3500 | >20 | | |
| 10 | 264 | 23 | 156 | 1.6 | | |
| 11 | 230 | 4.2 | 1130 | 60 | | |
| 12 | 920 | 3.0 | 3700 | 45 | | |
| 13 | >25 | >2 | >60 | >3 | | |
| 14 | 7300 | 1.7 | <14400 | <10 | | |
| 15 | 6100 | 1.1 | 14000 | 2 | | |
| 17 | 1790 | 3.2 | 3340 | 14 | | |
| 18 | 3 | — | — | — | | |
| 19 | >100 | ca. 3 | >300 | >5 | | |
| 20 | 150 | 14 | 1200 | 36 | | |
| 21 | >240 | >2 | >300 | >3 | | |
| 22 | 426 | 3.2 | 3600 | 130 | | |
| 23 | 97 | 1.4 | >450 | >1 | | |
| 24 | 62 | 2.0 | >273 | >1 | | |

The following Examples 1 to 3 show that compound 1 (referred to therein as SN23862) is reductively activated by bacterial nitroreductase enzymes.

The alkylating agent 5-(aziridin-1-yl)-2,4-dinitrobenzaride (hereinafter designated CB 1954) has been known, almost for 20 years, as an interesting experimental compound of unique selectivity. Although CB 1954 is structurally quite closely related to numerous other known alkylating agents which have a relatively broad range of activity, CB 1954 exhibits considerable activity against the Walker tumour cells in vivo or in vitro but was thought to be virtually inactive against other tumours.

It was recently discovered that the selectivity of CB 1954 arose from the fact that it was not an anti-tumour agent per se but was a prodrug for an anti-tumour agent generated from CB 1954 by a nitroreductase enzyme found in the Walker cell. This nitroreductase from the Walker cell was subsequently shown to be an enzyme known from other sources which was an AND(P)H dehydrogenase (quinone) classified as EC.1.6.99.2, see Robertson et al. *J. Biol. Chem.* 261, 15794–15799 (1986).

In the course of the previous investigations with CB 1954,it was found that the Walker cell enzyme EC.1.6.99.2 had the ability to reduce the 4-nitro group of CB 1954 to the corresponding hydroylamine and that it was the resulting 5-(aziridin-1-yl)-2-nitro-4-hydroxylamino-benzamide that was the active anti-tumour agent.

PCT Application PCT/GB92/01947 of Cancer Research Campaign Technology Limited describes new nitroreductases, obtainable from bacterial sources, for example from *Escherichia coli* and from *Bacillus amyloliquifaciens*, that are of interest in that not only are they capable of converting CB 1954 into an active anti-tumour agents but also, unlike EC.1.6.99.2. capable of converting CB 1954 analogues which are also prodrugs into active anti-tumour agents.

As is more particularly described in PCT Application PCT/GB92/01947 the use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent.

EXAMPLE 1

The effect of SN23862 on the survival of V79 cells in the presence of the *E. coli* nitroreductase. all treatments were for 2 hours at 37° C. and the cells were then plated out for their resulting colony forming ability. The nitroreductase concentration was 2 μg/ml and NADH was used as a co-factor. The initial cell density was $2 \times 10^5$ /mL.

| TREATMENT | % SURVIVAL | % DRUG REDUCTION |
|---|---|---|
| CONTROL | 100 | — |
| +500 μM NADH | 100 | — |
| +50 μM SN23862 | 100 | <1.0 |
| +NADH + SN23862 | 100 | <1.0 |
| +Nitroreductase | 94 | — |
| +NR + 50 μM SN23862 | 99 | <1.0 |
| +NR + SN23862 + 500 μM NADH | 0.007 | 95 |

EXAMPLE 2

The effect of SN23862 on the survival of V79 cells in the preence of the *B. amyloliquifaciens* nitroreductase. All treatments were for 2 hours at 37° C. and the cells were then plated out for their resulting colony forming ability. The nitroreductase concentration was 7.45 μg/ml and NADII was ised as a co-factor. The initial cell density was $2 \times 10^5$ /mL.

| TREATMENT | % SURVIVAL | % DRUG REDUCTION |
|---|---|---|
| CONTROL | 100 | — |
| +500 μM NADH | 120 | — |
| +50 μM SN23862 | 110 | <1.0 |
| +NADH + SN23862 | 115 | <1.0 |
| +Nitroreductase (BA) | 96.8 | — |
| +BA + 50 μM SN23862 | 110 | <1.0 |
| +BA + SN23862 + 500 μM NADH | 6.0 | >95 |

EXAMPLE 3

The effect of SN23862 on the survival of V79 or Mawi cells in the presence of the *E. coli* nitroreductase: A5B7 F(ab)$_2$ conjugate. All treatments were for 2 hours at 37° C. and the cells were then plated out for their resulting colony forming ability. The conjugate concentration was 81 μg/ml (euivalent to 5.2 μg/ml nitroreductase) and NADII was used as a co-factor. The initial cell density was $2 \times 10^5$/mL. No attempt was made to remove unbound conjugate.

| TREATMENT | % SURVIVAL MAWI Cells | % SURVIVAL V79 Cells | % DRUG REDUCTION |
|---|---|---|---|
| CONTROL | 100 | 100 | — |
| +500 μM NADH | 104.6 | 94.6 | — |
| +50 μM SN23862 | 90.9 | 94.3 | <1.0 |
| +NADH + SN23862 | 93.1 | 80.4 | <1.0 |
| +Conjugate (CG) | 85.5 | 85.8 | — |

-continued

| TREATMENT | % SURVIVAL | | % DRUG REDUCTION |
|---|---|---|---|
| | MAWI Cells | V79 Cells | |
| +CG + 50 µM SN23862 | 94.6 | 73.5 | <1.0 |
| +CG + SN23862 + 500 µM NADH | 0.014 | 0.003 | >99 |

The accompanying

Figure 1:
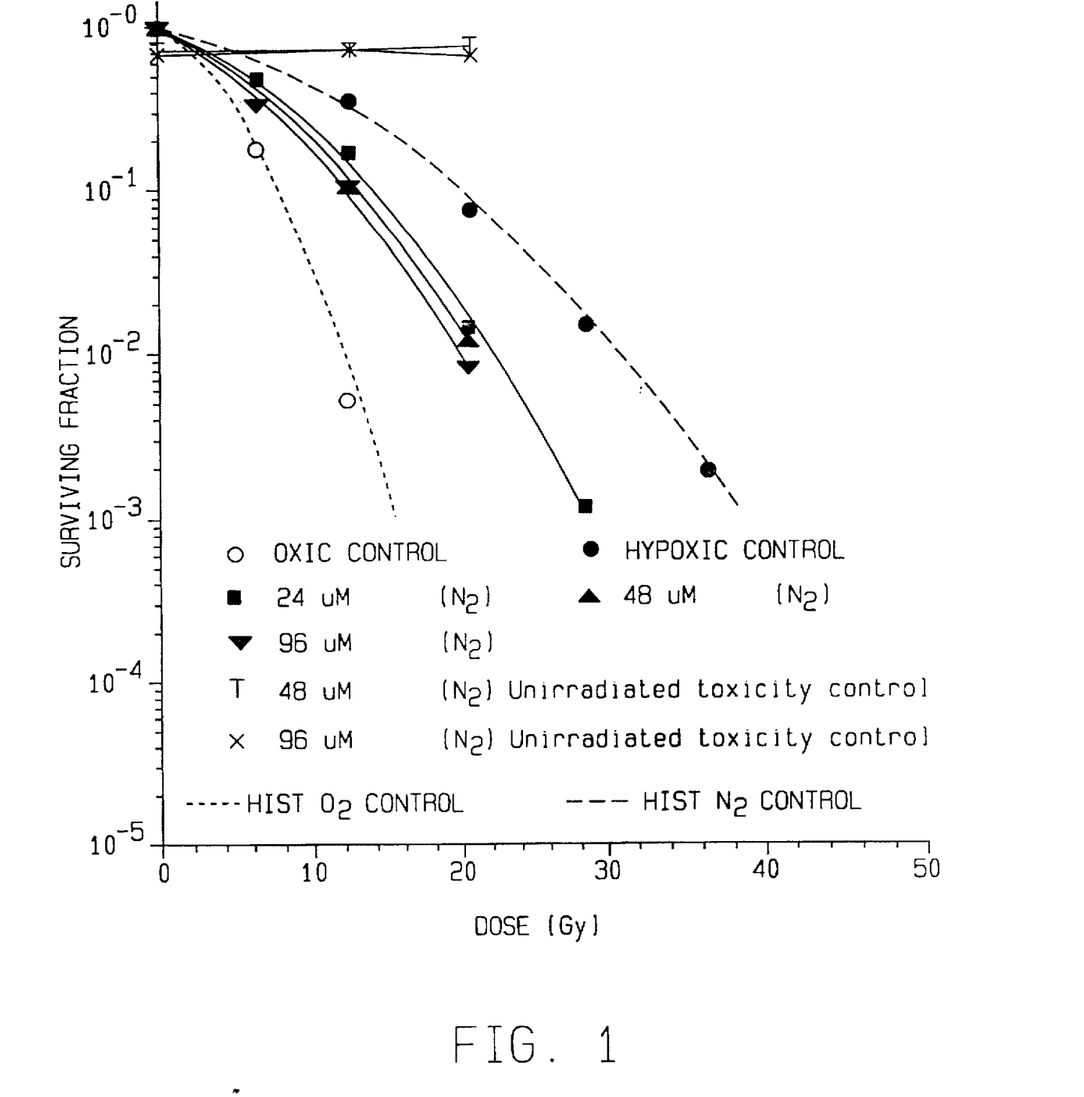
FIG. 1 shows radiosensitising properties of compound 1.

The radiosensitising efficiency of compound 1 has been assessed in stirred suspensions of AA8 cells under hypoxic conditions using gamma irradiation (cobalt 60) at a dose rate of 2.2 Gy/min at 37° C. Drug and cells were mixed under hypoxic conditions 30 min before irradiation. Radiosensitisation of hypoxic cells was observed (FIG. 1). The concentration for an enhancement ratio (ratio of radiation doses for 10% survival with and without drug) of 1.6 ($C_{1.6}$) was approximately 100 µM, and this extent of sensitisation was observed in the absence of drug toxicity (FIG. 1). Compound 1 is therefore a hypoxic cell radiosensitiser as well as a hypoxia-selective cytotoxin.

It is clear from the data of Table 2, Examples 1 to 3 and FIG. 1 that the examples of the nitroaniline derivatives of general formula (I) listed in Table 2 include compounds which are active as cytotoxic agents, and which have the additional capability of being reductively activated by both mammalian tumour cells and bacterial nitroreductase enzymes, and are therefore suitable as prodrugs. The compounds are selectively toxic to hypoxic tumour cells, and therefore useful as anticancer drugs. The compounds are capable of sensitising hypoxic cells in vitro to ionising radiation and thus are suitable as hypoxic cell radiosensitisers.

The present invention therefore also provides pharmaceutical compositions having antitumour and radiosensitising activity and comprising at least one compound represented by the general formula (I), and one or more pharmaceutically-acceptable carriers or diluents.

The present invention further provides the use of at least one compound represented by the general formula (I) for the manufacture of pharmaceutical compositions for the treatment of tumours, in particular cancers.

When the compounds of formula (I) are used as reductively-activated prodrugs for cytotoxins, they can be used in association with nitroreductase enzymes, including the nitroreductases described in Application PCT/GB92/01947, and so provide a system of cancer chemotherapy where the extent of exposure of the patient to the cytotoxic agent is limited, so far as possible, to those regions where there is the inter-reaction between the prodrug and the nitroreductase.

The most or one of the most convenient ways of utilising such a system of cancer chemotherapy is to conjugate the nitroreductase to a targetting agent such as a monoclonal antibody that will bind with a tumour-associated antigen.

The term "monoclonal antibody" will be understood by those of skill in the art not simply to refer to antibodies produced by traditional hybridoma techniques, but also to cover antibodies and variants thereof produced by recombinant means. These include, for example, humanised antibodies such as those with a constant region from a human antibody grafted onto a non-human antibody variable region (see for example EP-A-0 120 694), chimeric antibodies such as those with non-human complementarity determining regions (CDRs) grafted into a human variable region framework (see for example EP-A-0 239 400) and single, chain antibodies. Fragments of such monoclonal antibodies which retain their target binding activity are also included by the general term "monoclonal antibody". This includes Fab' and F(ab')$_2$ fragments.

The selection of monoclonal antibody will clearly be influenced by the nature of the target tumour but for the purposes of illustration, reference may be made to the anti-CEA antibody $A_5B_7$.

With this system, it is possible in a course of cancer chemotherapy to administer to the patient requiring the treatment the nitroaniline compound which is the prodrug for a cytotoxic compound and the enzyme/targeting agent conjugate. The prodrug and the conjugate can be administered simultaneously but it is often found preferable, in clinical practice, to administer the enzyme/agent conjugate before the prodrug; e.g. up to 72 hours before, in order to give the enzyme/agent conjugate an opportunity to localise in the region of the tumour target. By operating in this way, when the prodrug is administered, conversion of the prodrug to the cyrotoxic agent tends to be confined to the regions where the enzmye/agent conjugate is localised, i.e. the region of the target tumour and damage to healthy cells caused by the premature release of the cytotoxic agent is minimised.

The degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the nitroreductase which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

The exact dosage regime will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and the enzyme/agent conjugate and administration by the intravenous route is frequently found to be the most practical.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets troches, capsules, elixirs, suspensions, syrups wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 mcg of active compound.

The tablets, troches, pills, capsules and the like may also contain tile following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisns.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability, exists. It must be stable under the conditions of manufacture and storage and must be preserved against be contaminating action of microorganisms such as bacteria and fungi. The carrier can be a solvent or dispersion medium containing, for example, water, ethanol, polyol (for example, elycerol, propylene glycol, and liquid polyethylene glycol, and the like), suitable mixtures thereof and vegetable oils. The proper fluidity can be maintained, for example; by the use of a coating such as lecithin, by the maintenance of the required particle size in the case of dispersions and by the use of surfactants. The prevention of the action of microorganisms can be brought about bv various antibacterial and antifungal agents, for example, parabens, clorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about 1 to about 30 mg being preferred. Expressed in proportions, the active compound is generally present, in from about 0.1 to 400 mg/ml of carrier. In the case of compositions containing supplementary active ingredients, the dosages are determined bv reference to the usual dose and manner of administration of the said ingredients.

What we claim is:

1. A compound represented by the formula (I), where $NO_2$ is in the 2-position, R represents $CONHCH_2CH_2NMe_2$, A represents $4-NO_2$ and B represents $5-N(CH_2CH_2Cl)_2$.

2. A compound represented by the formula (I), (I)

where NO₂ is in the 2-position, R represents CONHCH₂CH₂N()Me₂, A represents 4-NO₂ and B represents 5-N(CH₂CH₂Cl)₂.

3. A compound represented by the formula (I), (I)

where NO₂ is in the 2-position, R represents CONHCH₂CH₂NMe₂, A represents 6-NO₂ and B represents 5-N(CH₂CH₂Cl)₂.

4. A compound represented by the formula (I), (I)

where NO₂ is in the 3-position, R represents CONHCH₂CH₂NMe₂, A represents 5-NO₂ B represents 2-N(CH₂CH₂Cl)₂.

* * * * *